United States Patent [19]

Amato et al.

[11] 4,362,726
[45] Dec. 7, 1982

[54] SUBSTITUTED-1,2,5-THIADIAZOLE-1-OXIDE COMPOUNDS, COMPOSITIONS AND USE

[75] Inventors: Joseph S. Amato, Brooklyn, N.Y.; Sandor Karady, Mountainside; Leonard M. Weinstock, Belle Mead, both of N.J.

[73] Assignee: Merck & Co., Inc., Rahway, N.J.

[21] Appl. No.: 257,062

[22] Filed: Apr. 24, 1981

[51] Int. Cl.$^3$ ............... C07D 413/04; C07D 417/04; A61K 31/425; A61K 31/535
[52] U.S. Cl. ............... 424/248.51; 424/250; 424/267; 424/270; 544/134; 544/367; 546/209; 548/135
[58] Field of Search ............ 544/134, 367; 546/209; 548/135; 424/248.51, 250, 267, 270

[56] References Cited

U.S. PATENT DOCUMENTS 4,094,986  1/1978  Rokach et al. ............... 424/270

FOREIGN PATENT DOCUMENTS 1961864  6/1971  Fed. Rep. of Germany .
2852869  6/1980  Fed. Rep. of Germany .
8004967  3/1981  Netherlands .
2067987  5/1981  United Kingdom .

OTHER PUBLICATIONS

Horning et al., Canadian Journal of Chemistry, 51 2349 (1973).
Deyrup et al., Journal of Organic Chemistry, 42 1015 (1977).
Rokach et al., Journal of Organic Chemistry, 44 1118 (1979).
Wen et al., *J. Org. Chem.*, vol. 40, (1975), pp. 2743-2746.
Tocco et al., *Chem. Abstracts*, vol. 93, (1980), No. 179,300t; Chem. Substance Index, p. 6435CS.

*Primary Examiner*—Robert W. Ramsuer
*Attorney, Agent, or Firm*—Ernest V. Linek; Martin L. Katz

[57] ABSTRACT

Substituted-1,2,5-thiadiazole-1-oxides, their preparation and pharmaceutical use as elastase inhibitors are disclosed.

20 Claims, No Drawings

SUBSTITUTED-1,2,5-THIADIAZOLE-1-OXIDE COMPOUNDS, COMPOSITIONS AND USE

BACKGROUND OF THE INVENTION

Considerable work has been done on the chemistry of 3-substituted-1,2,5-thiadiazole compounds. See for example, Horning et al. Canadian *Journal of Chemistry* 51 2349 (1973) and Deyrup et al. *Journal of Organic Chemistry* 42 1015 (1977). However, little work has been done on 2-substituted-1,2,5-thiadiazoles of the type shown for example in Rockach et al., *Journal of Organic Chemistry* 44 1118 (1979).

SUMMARY OF THE INVENTION

This invention is directed to substituted-1,2,5-thiadiazole-1-oxide compounds, their preparation and pharmaceutical use. These compounds have pharmacological activity as elastase inhibitors.

DETAILED DESCRIPTION

This invention is directed to substituted-1,2,5-thiadiazole-1-oxide compounds represented by the formula:

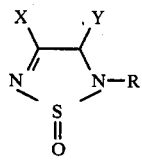

wherein:
(a) Y is either O or NH; and
(b) X is lower-alkoxy, benzyloxy, phenyllower-alkoxy, N-lower-alkyl amino, N,N-disubstituted lower-alkylamino, a 6-membered heterocyclic ring which may also contain an oxygen, or N—R″ heteroatom, said heterocyclic ring selected from morpholine, piperidine, piperazine, N-lower-alkyl piperazine, and pyrrolidine wherein R″ is hydrogen or lower-alkyl
(c) R is alkyl, benzyl, phenyllower-alkyl, alkylcarbonyl, benzoyl, monohalogen-substituted-benzoyl, lower-alkyl-substituted anilino carbonyl, N-lower-alkylcarbamoyl, lower-alkoxycarbonyl, lower-alkylcarbonyllower-alkyl, phenylcarbonyllower-alkyl, monohalogen-substituted-phenylcarbonyl-lower-alkyl, and lower-alkoxycarbonyllower-alkyl.

As employed in the instant application, the term "alkyl" is intended to include those alkyl groups, of either a straight or branched configuration, which contain from 1 to 12 carbon atoms.

The term "lower-alkyl" is intended to include those alkyl groups, of either a straight or branched configuration which contain from 1 to 5 carbon atoms.

The term "lower-alkoxy" is intended to include those alkoxy groups of either a straight or branched configuration which contain from 1-5 carbon atoms. Examples of such alkoxy groups are methoxy, ethoxy, propoxy, isopropoxy, butoxy, sec-butoxy, tert-butoxy, pentoxy, and the like.

The term "monohalogen" is intended to represent single substitution of hydrogen by chlorine, bromine and/or iodine.

A preferred group of compounds is represented by the formula:

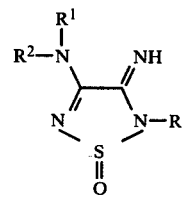

More preferred are the compounds of formula II where R is lower-alkyl and $R^1$ and $R^2$ are combined to form a morpholine or piperazine ring system.

Certain clinical symptoms found in pancreatitis, emphysema and rheumatoid arthritis are believed to be caused by uncontrolled amounts of elastase, a proteolytic enzyme in the affected tissues.

The compounds of the present invention are useful as pharmaceuticals, especially as elastase inhibitors.

For treatment of symptoms caused by uncontrolled amounts of elastase in patients, the compounds of the present invention are administered in effective amounts in appropriate dosage forms, via an acceptable pharmaceutical carrier.

Any suitable route of administration may be used such as oral, parenteral, intramuscular and the like. The appropriate dosage forms are exemplified by tablets, troches, dispersions, suspensions, solutions, capsules and the like for oral administration; suspensions, solutions, emulsions and the like for parenteral administration.

The daily dosage for inhibition of elastase may range from about 15 mg to about 50 mg, preferably about 20 mg.

The pharmaceutical compositions containing the compounds of the present invention comprise another embodiment of the instant invention. These compositions are made using conventional procedures and ingredients, as required by those skilled in the art.

The compounds of the present invention may be prepared by any convenient process.

One such process is illustrated by the following reaction equation:

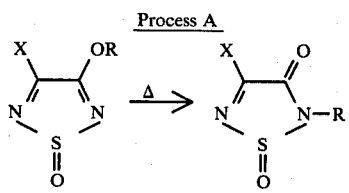

In process A, for example, 3-ethoxy-4-piperazino-1,2,5-thiadiazole-1-oxide is heated from 150° C. to 200° C. as a melt for 20 to 30 minutes. The product isolated is 2-ethyl-4-piperazino-1,2,5-thiadiazole-3-one-1-oxide.

Another process for preparing the compounds of the present invention is illustrated by the following equations:

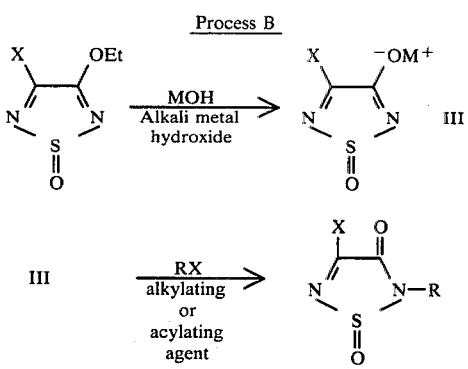

In process B, for example, 3-ethoxy-4-morpholino-1,2,5-thiadiazole-1-oxide is treated with an alkali metal hydroxide such as potassium hydroxide in an alcohol and the potassium salt is isolated. The potassium salt is reacted with an alkylating or acylating reagent such as benzyl bromide in a suitable solvent such as DMF. The alkylation or acylating is generally carried out at room temperature. The isolated product is 2-benzyl-4-morpholino-1,2,5-thiadiazole-3-one-1-oxide.

A third process for preparing compounds of the present invention is similar to Process B:

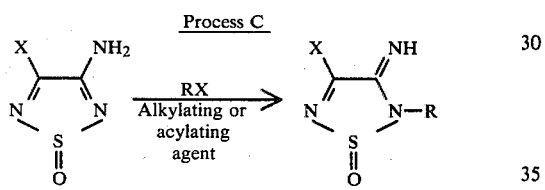

In Process C, for example, 3-amino-4-morpholino-1,2,5-thiadiazole-1-oxide is treated with 4-methylphenylisocyanate in a suitable solvent such as THF. The reaction is generally carried out at room temperature. The isolated product is 3-imino-N-(4-methylphenyl)-4-morpholino-1,2,5-thiadiazole-2-carboxamide-1-oxide.

The following examples illustrate the preparation of the compounds of formula I using the processes described above. Unless otherwise specified, all temperatures are in degrees Celsius.

These examples are provided in order that the present invention might be more fully understood. They are not to be construed as limiting the invention in any manner.

EXAMPLE I 2-ethyl-4-piperazino-1,2,5-thiadiazole-3-one-1-oxide (A)

One gram of 3-ethoxy-4-piperazino-1,2,5-thiadiazole-1-oxide is heated under nitrogen at 210° for 30 minutes. The solid residue (A) is purified by chromatography on silica gel (100 g) using a methylene chloride-ethyl acetate gradient. IR(CHCl$_3$); 1690, 1590 cm$^{-1}$. Proton NMR (CDCl$_3$, 60 MHz), δ1.35 (t, 3H, J=8 Hz, CH$_3$), 1.8 (s, 6H, CH$_2$CH$_2$CH$_2$), 3.65 (q, 2H, J=8 Hz, N—CH$_2$—) 3.8 and 4.4 (s, 2H, NCH$_2$).

EXAMPLE II 2-benzyl-4-morpholino-1,2,5-thiadiazole-3-one-1-oxide (B)

One gram of 3-benzyloxy-4-mopholino-1,2,5-thiadiazole-1-oxide is heated under nitrogen at 150° for 20 minutes. The solid residue (B) is purified by chromatography on silica gel (100 g) using a methylene chloride-ethyl acetate gradient. The product (B) is recrystallized from ether and melts at 95°–98°. Proton NMR (CDCl$_3$, 60 MHz); δ3.7 (m, 6H, CH$_2$O and CH$_2$N), 4.3 (m, 2H, NCH$_2$), 4.7 (center of AB, 2H, J=15 Hz, OCH$_2$) and 7.3 (s, 2H, PhCH$_2$).

EXAMPLE III (a) 3-Hydroxy-4-morpholino-1,2,5-thiadiazole-1-oxide potassium salt (C)

A solution of 1.15 gram 3-ethoxy-4-morpholino-1,2,5-thiadiazole-1-oxide in 6 ml of 0.85 M potassium hydroxide in methanol is allowed to stand at room temperature for 30 minutes. The precipitated product (C) is isolated by filtration to yield 1 gram white solid.

Anal. Calcd. for C$_6$H$_8$N$_3$O$_3$SK: C, 29.86; H, 3.34; N, 17.41; S, 13.29. Found: C, 29.83; H, 3.07; N, 17.38; S, 13.35.

(b) 2-benzyl-4-morpholino-1,2,5-thiadiazole-3-one-1-oxide (D)

A solution of 4.0 grams of the potassium salt (C) formed in step (a) and 3 ml benzyl bromide in 10 ml DMF is allowed to stand at room temperature for 5 hours. Water is then added to induce precipitation and the product is collected. The 4.6 grams of crude product (D) is recrystallized from ether and hexane. The solid material (D) has a melting point of 98°–99°.

The product was identical in NMR, IR and tlc to product (B) of Example II.

EXAMPLE IV 2-(p-chlorobenzoyl)-4-morpholino-1,2,5-thiadiazole-3-one-1-oxide (E)

To a slurry of 2.3 grams of the potassium salt (C) from Example III(a) in 10 ml methylene chloride and 5 ml DMF is added 1.5 ml p-chlorobenzoylchloride. This mixture is allowed to stir for 1 hour at room temperature. After this, saturated sodium bicarbonate solution is added and the product is extracted into methylene chloride. The organic layer is dried and concentrated in vacuo. The crude product (E) is crystallized from ether and hexane to yield 2 grams of the title compound.

IR (CHCl$_3$); 1740, 1680 and 1610 cm$^{-1}$. Mass spectrum; m/e 341 (M$^+$), 292 (M—SO).

EXAMPLE V 2-(p-chlorophenacyl)-4-morpholino-1,2,5-thiadiazole-3-one-1-oxide (F)

To a slurry of 2.3 grams of the potassium salt from Example III(a) in 10 ml methylene chloride and 5 ml DMF is added 1.5 ml p-chlorophenacylbromide. This mixture is allowed to stir for 1 hour at room temperature. After this, saturated sodium bicarbonate solution is added and the product is extracted into methylene chloride. The organic layer is dried and concentrated in vacuo. The crude product (F) is recrystallized from ethyl acetate.

IR (CHCl$_3$); 1715, 1700 cm$^{-1}$. Proton NMR (CDCl$_3$, 60 MHz); δ3.8 (m, 6H, N—CH$_2$ and O—CH$_2$), 4.4 (m, 2H, O—CH$_2$), 4.95 (center of AB, 2H, J=18 Hz, N—CH$_2$—CO) and 7.7 (center of AB, 4H, C$_6$H$_4$).

EXAMPLE VI

3-Imino-N(4-methylphenyl)-4-morpholino-1,2,5-thiadiazole-2-carboxamide-1-oxide (G)

A mixture of 2 grams of 3-amino-4-morpholino-1,2,5-thiadiazole-1-oxide and 1.4 ml of 4-methylphenylisocyanate in 50 ml THF is stirred for 48 hours at room temperature. Ether is added to precipitate the product (G) which is collected by filtration.

IR (Nujol); 1650, 1580, 1540 cm$^{-1}$. Mass spectrum; m/e 335

Anal. Calcd. for $C_{14}H_{17}N_5O_3S$: C, 50.14; H, 5.11; N, 20.88; S, 9.56; Found: C, 49.56; H, 5.14; N, 20.88; S, 9.06.

What is claimed is:

1. Compounds having the formula:

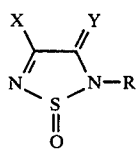

wherein:
(a) Y is either O or NH; and
(b) X is a 6-membered nitrogen containing heterocyclic ring which may also contain an oxygen or N—R″ heteroatom, said heterocyclic ring selected from morpholine, piperidine, piperazine and N-lower-alkyl piperazine, wherein R″ is hydrogen or lower-alkyl; and
(c) R is alkyl, benzyl, monohalogen-substituted-benzoyl, lower-alkyl-substituted anilino carbonyl, N-lower-alkyl carbamoyl, lower-alkoxy carbonyl, lower-alkylcarbonyllower-alkyl, phenylcarbonyllower-alkyl, monohalogen-substituted phenylcarbonyllower-alkyl and lower-alkoxy-carbonyllower-alkyl.

2. The compounds of claim 1 wherein Y is oxygen.

3. The compound of claim 1 wherein X is morpholine.

4. The compounds of claim 3 wherein R is lower alkyl.

5. The compound of claim 1, 2-ethyl-4-piperazino-1,2,5-thiadiazole-3-one-1-oxide.

6. The compounds of claim 3 wherein R is benzyl.

7. The compound of claim 3, 2-benzyl-4-morpholino-1,2,5-thiadiazole-3-one-1-oxide.

8. The compounds of claim 3 wherein R is monohalogen-substituted-benzoyl.

9. The compound of claim 3, 2-(p-chlorobenzoyl)-4-morpholino-1,2,5-thiadiazole-3-one-1-oxide.

10. The compounds of claim 3 wherein R is monohalogen-substituted-phenylcarbonyllower-alkyl.

11. The compound of claim 3, 2-(p-chlorophenacyl)-4-morpholino-1,2,5-thiadiazole-3-one-1-oxide.

12. Compounds having the formula:

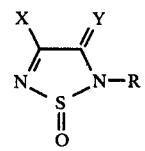

wherein:
(a) Y is NH; and
(b) X is a 6-membered nitrogen containing heterocyclic ring which may also contain an oxygen or N—R″ heteroatom, said heterocyclic ring selected from morpholine, piperidine, piperazine and N-lower-alkyl piperazine, wherein R″ is hydrogen or lower-alkyl; and
(c) R is alkyl, benzyl, monohalogen-substituted-benzoyl, lower-alkyl-substituted anilino carbonyl, N-lower-alkyl carbamoyl, lower-alkoxy carbonyl, lower-alkylcarbonyllower-alkyl, phenylcarbonyllower-alkyl, monohalogen-substituted phenylcarbonyllower-alkyl and lower-alkoxy-carbonyllower-alkyl.

13. The compounds of claim 12 wherein X is morpholine or piperazine.

14. The compounds of claim 12 wherein R is lower-alkyl.

15. The compounds of claim 12 wherein R is benzyl.

16. The compound of claim 12, 3-imino-N-(4-methylphenyl)-4-morpholino-1,2,5-thiadiazole-2-carboxamide-1-oxide.

17. The compounds of claim 12 wherein R is monohalogen-substituted-benzoyl.

18. The compounds of claim 12 wherein R is monohalogen-substituted-phenyl carbonyl lower-alkyl.

19. A pharmaceutical composition useful in treating pancreatitis, emphysema, rheumatoid arthritis or inhibiting elastase containing an effective amount of a compound of claim 1 in a pharmaceutical carrier.

20. A method of inhibiting uncontrolled amounts of elastase in a patient which comprises administering an effective amount of a compound of claim 1.

* * * * *